US008814846B2

(12) United States Patent
Horton et al.

(10) Patent No.: US 8,814,846 B2
(45) Date of Patent: Aug. 26, 2014

(54) DUAL LUMEN CATHETER AND METHOD FOR MINIMALLY INVASIVE ENDOLUMINAL SURGERY

(75) Inventors: Kenneth W. Horton, South Glastonbury, CT (US); Peter Hathaway, Lebanon, CT (US)

(73) Assignee: Covidien LP, Mansfield, MA (US)

( * ) Notice: Subject to any disclaimer, the term of this patent is extended or adjusted under 35 U.S.C. 154(b) by 1094 days.

(21) Appl. No.: 12/267,723

(22) Filed: Nov. 10, 2008

(65) Prior Publication Data

US 2009/0124999 A1 May 14, 2009

Related U.S. Application Data

(60) Provisional application No. 60/987,444, filed on Nov. 13, 2007.

(51) Int. Cl.
*A61M 31/00* (2006.01)

(52) U.S. Cl.
USPC ........................................................ 604/514

(58) Field of Classification Search
USPC .................. 606/185; 604/164.01, 514, 93.01, 604/96.01, 99.04, 516, 264; 128/898
See application file for complete search history.

(56) References Cited

U.S. PATENT DOCUMENTS

| 5,569,215 A | * | 10/1996 | Crocker ......................... 604/264 |
| 2001/0049497 A1 | * | 12/2001 | Kalloo et al. ............. 604/164.01 |
| 2007/0123840 A1 | * | 5/2007 | Cox ............................... 604/514 |

FOREIGN PATENT DOCUMENTS

| EP | 0 191 599 | 8/1986 |
| EP | 0 333 308 | 9/1989 |
| EP | 1 462 143 | 9/2004 |
| WO | WO 99/55384 | 11/1999 |

OTHER PUBLICATIONS

European Search Report for EP 08253689.7-2319 date of completion is Feb. 9, 2009 (3 pages).

* cited by examiner

*Primary Examiner* — Katherine M Shi (57) ABSTRACT

A duel lumen catheter is provided for use in minimally invasive surgery. The catheter generally includes a first tube defining an operative lumen and a second tube terminating proximally of the first tube and defining an inflation lumen. In one embodiment, the first and second tubes are concentric. In an alternative embodiment, the first and second tubes are separate and extend parallel to each other. The first and second tubes are provided with inflation ports adjacent their respective distal ends. There is also provided a method for performing minimally invasive surgery by inserting the catheter through the esophagus of a patient, insufflating the stomach and performing a surgical operation through the catheter and external to the stomach.

4 Claims, 7 Drawing Sheets

DUAL LUMEN CATHETER AND METHOD FOR MINIMALLY INVASIVE ENDOLUMINAL SURGERY

CROSS-REFERENCE TO RELATED APPLICATIONS

This application claims the benefit of and priority to U.S. Provisional Patent Application No. 60/987,444, filed Nov. 13, 2007, the entire disclosure of which is incorporated by reference herein.

BACKGROUND

1. Technical Field

The present disclosure relates to a dual lumen catheter having an operative passageway for use in minimally invasive endoluminal surgery. More particularly, the present disclosure relates to a duel lumen catheter and method of performing minimally invasive endoluminal surgery through the stomach of a patient.

2. Background of Related Art

Surgeons are constantly searching for ways of performing surgical procedures within the body of a patient in a minimally invasive manner. This is desirable in order to reduce scarring, as well as, to shorten the healing or recuperation time of a patient from the surgery. As an example, one way to accomplish this is through the use of trans-luminal or trans-gastric surgery. In these methods, the surgeon inserts various instruments through the esophagus of the patient to gain access to the stomach. Once the stomach has been reached, and opening in the gastric wall is accomplished to gain access to the peritoneal cavity and perform various surgeries, such as, for example, hernia repair, etc.

In these surgical procedures the peritoneal cavity is typically insufflated to provide a visualization area and\or working room for the surgical instruments. However, a potential problem exists when the peritoneal cavity is pressurized in that the pressure created within the peritoneal cavity pushes down on the stomach thereby flattening the stomach and making it difficult to manipulate surgical and/or visualization instruments through the interior of the stomach.

Thus, it would be desirable to provide a catheter and method of performing a trans-gastric surgery without the attendant problem of stomach collapse due to pressurization of the adjacent peritoneal cavity.

SUMMARY

There is disclosed a dual lumen catheter for use in minimally invasive surgery. The catheter generally includes a hub, a first tube extending through the hub and defining an operative lumen from the hub to a distal end of the first tube. A second tube extends parallel to the first tube and sealed at its distal end. The distal end of the second tube is positioned proximally of the distal end of the first tube, wherein the second tube defines an inflation lumen.

In one embodiment the second tube is positioned concentrically about the first tube. The second tube includes inflation ports positioned adjacent the distal end of the second tube. A seal is positioned between the first and second tubes to seal the distal end of the second tube. A valve system is in fluid communication with the inflation lumen such that the valve system applies a source of fluid through the inflation lumen.

The first tube includes ports positioned adjacent the distal end of the first tube and includes a cutting edge at the distal end thereof.

In an alternative embodiment, the first and second tubes extend through and distally of a support tube associated with the hub. A seal is positioned within the support tube and about the first and second tubes to seal interior of the support tube. The second tube includes inflation ports positioned adjacent the distal end of the second tube.

There is also disclosed a method of performing a minimally invasive procedure utilizing a dual lumen catheter. A catheter is provided having a first tube defining an operative lumen and a second tube, parallel to the first tube, defining an inflation lumen and terminating proximally of the distal end of the first tube. The catheter is inserted through the esophagus of a patient so as to position a distal end of the second tube within the stomach of a patient. The catheter is further advanced through the esophagus of a patient so as to position the distal end of the first tube outside of the stomach of the patient and a surgical operation is performed through the first tube and outside the stomach of the patient. The method further includes pressurizing the interior of the stomach by forcing a fluid through the inflation lumen and pressurizing an area outside of the stomach by forcing a fluid through the operative lumen.

In one use of the disclosed method the wall of the stomach is punctured with the distal end of the first tube.

DESCRIPTION OF THE DRAWINGS

Various embodiments of the presently disclosed dual lumen surgical catheter are disclosed herein with reference to the drawings, wherein.

DETAILED DESCRIPTION OF EMBODIMENTS

Embodiments of the presently disclosed dual lumen catheter and methods of endoluminal surgery will now be described in detail with reference to the drawings wherein like numerals designate identical or corresponding elements in each of the several views. As is common in the art, the term 'proximal" refers to that part or component closer to the user or operator, i.e. surgeon or physician, while the term "distal" refers to that part or component further away from the user.

Figure 1:
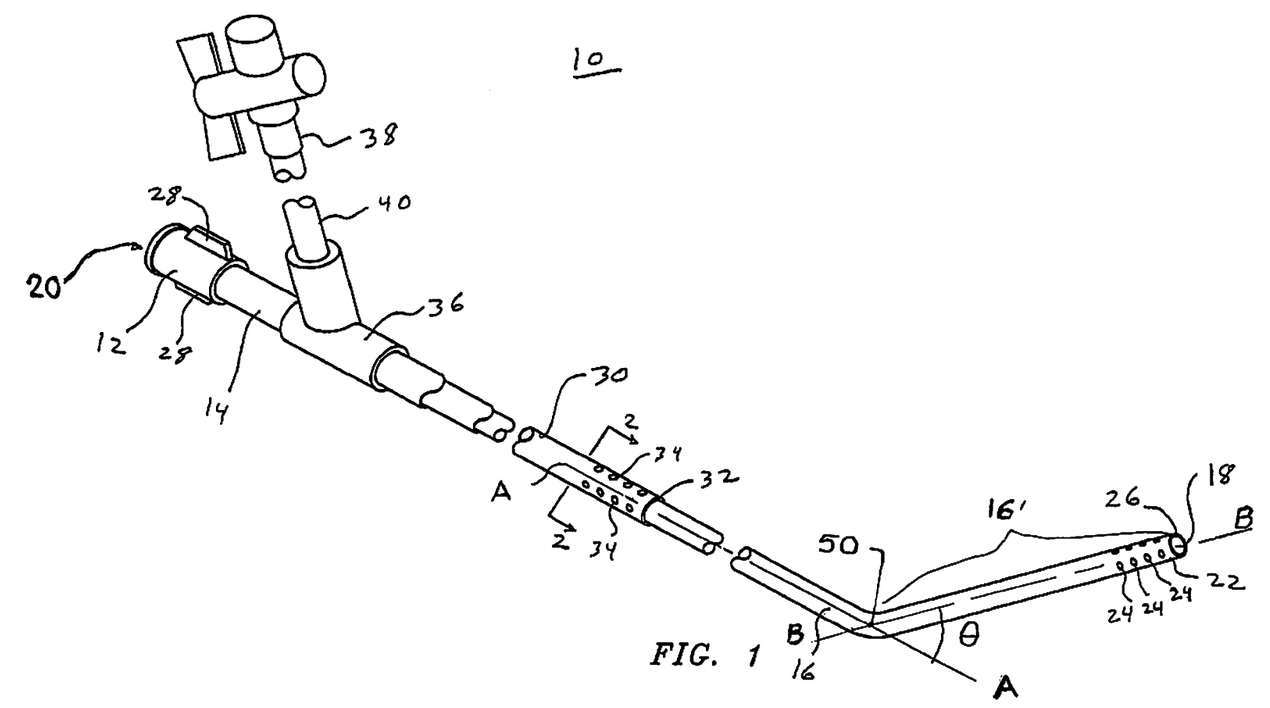
FIG. 1 is a perspective view of one embodiment of a duel lumen catheter for use in minimally invasive endoluminal surgery.

Referring to FIG. 1, there is disclosed a dual lumen catheter 10 particularly suitable for use in endoluminal surgery to support the stomach against collapse during surgical procedures. Catheter 10 generally includes a hub 12 having an outer sheath 14 extending distally from hub 12. An operative or inner tube 16 extends through hub 12 and sheath 14 and defines an operative lumen 18 extending from a proximal end 20 of inner tube 16 to a distal end 22 of inner tube 16. Operative lumen 18 in inner tube 16 provides an access passageway for surgical instruments as well as a fluid flow path for insufflation fluids to insufflate the peritoneal cavity. A plurality of insufflation ports 24 are provided adjacent distal end 22 of inner tube 16. Insufflations ports 24 are provided in case the instruments inserted through inner tube 16 block or seal the distal end of operative lumen 18 and thus prevent the flow of insufflation fluid out of the open end of operative lumen 18. Distal end 22 of inner tube 16 may additionally be provided with a cutting edge 26 to facilitate advancement of distal end 22 through a stomach wall and a peritoneal lining. In order to steer or direct catheter 10 through the body of a patient, hub 12 may be provided with a pair of wings 28. It should be noted that, however, other methods of steering catheter 10 to the body of a patient are contemplated here in such as, for example, various steerable guide wires etc. Additionally, other means or instruments known in the art may be provided to penetrate the stomach wall and peritoneal lining to provide access to the peritoneal cavity.

Catheter 10 is additionally provided with an outer tube 30 which extends partially over inner tube 16 to define a common longitudinal axis A-A. Outer tube 30 is sealed at a distal end 32 to inner tube 16. A plurality of inflation ports 34 are provided adjacent distal end 32 of outer tube 30 and are spaced proximally from insufflation ports 24 at a distal end 22 of inner tube 16. A T-collar 36 surrounds sheath 14 and is in fluid communication with inflation ports 34 at distal end 32 of outer tube 30. A valve system 38 is in fluid communication with T-collar 36 through a fluid tube 40. The inner tube 16 extends to a position 50 distal from the distal end 32 of the outer or insufflation tube 30 to define the common longitudinal axis A-A, the common longitudinal axis A-A extending at least to the position 50. The distal end 22 of the inner tube 16 defines a portion 16' of the inner tube 16 that extends at least from the position 50 to define an offset axis B-B with respect to the common longitudinal axis A-A. The offset axis B-B defines an offset angle θ with respect to the common longitudinal axis A-A of the inner tube 16. Consequently, the radially oriented insufflation ports 24 in proximity to the distal end 22 of the operative or inner tube 16 are positioned at a position that is offset from the radially oriented insufflation ports 34 at the distal end 32 of the outer or insufflation tube 30.

Figure 2:
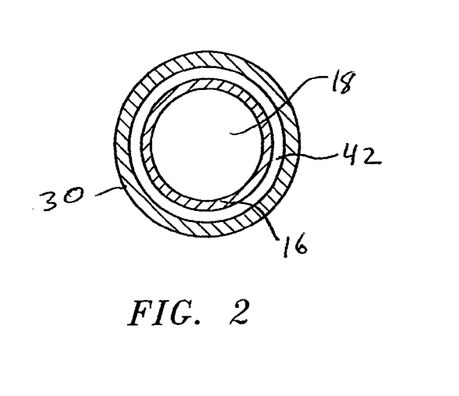
FIG. 2 is a cross-sectional view taken along the line 2-2 of FIG. 1.

Referring for the moment to FIG. 2, an inflation lumen 42 is defined between outer tube 30 and inner tube 16. As shown, inner tube 16 and outer tube 30, and thus operative lumen 18 and inflation lumen 42, are concentric. Inflation lumen 42 carries inflation fluid from valve system 38 to inflation ports 34 at a distal end of outer tube 30.

Figure 3:
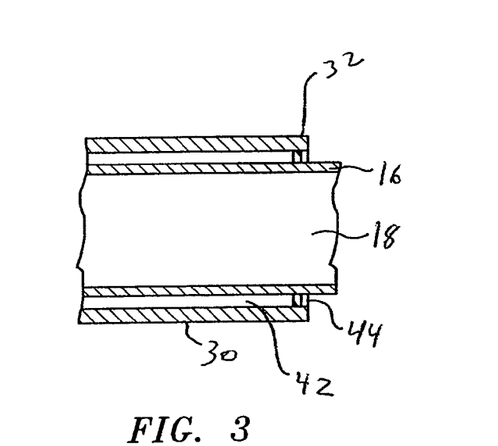
FIG. 3 is a cross-sectional view taken at the junction of the outer tubular member and the inner tubular member.

Referring to FIG. 3, and as noted hereinabove, distal end 32 of outer tube 30 terminates proximally of distal end 22 of inner tube 16 and is sealed to inner tube 16. Specifically, distal end 32 of outer tubes 30 is sealed to inner tube 16 by a circumferential seal 44. Seal 44 may be formed by gluing distal end 32 to inner tube 16 or may be provided as a separate member which is glued, welded, or otherwise affixed to distal end 32 and inner tube 16. Thus, fluid flowing from valve system 38 through inflation lumen 42 can only exit inflation ports 34 formed in distal end 32 of outer tube 30.

Figure 4:
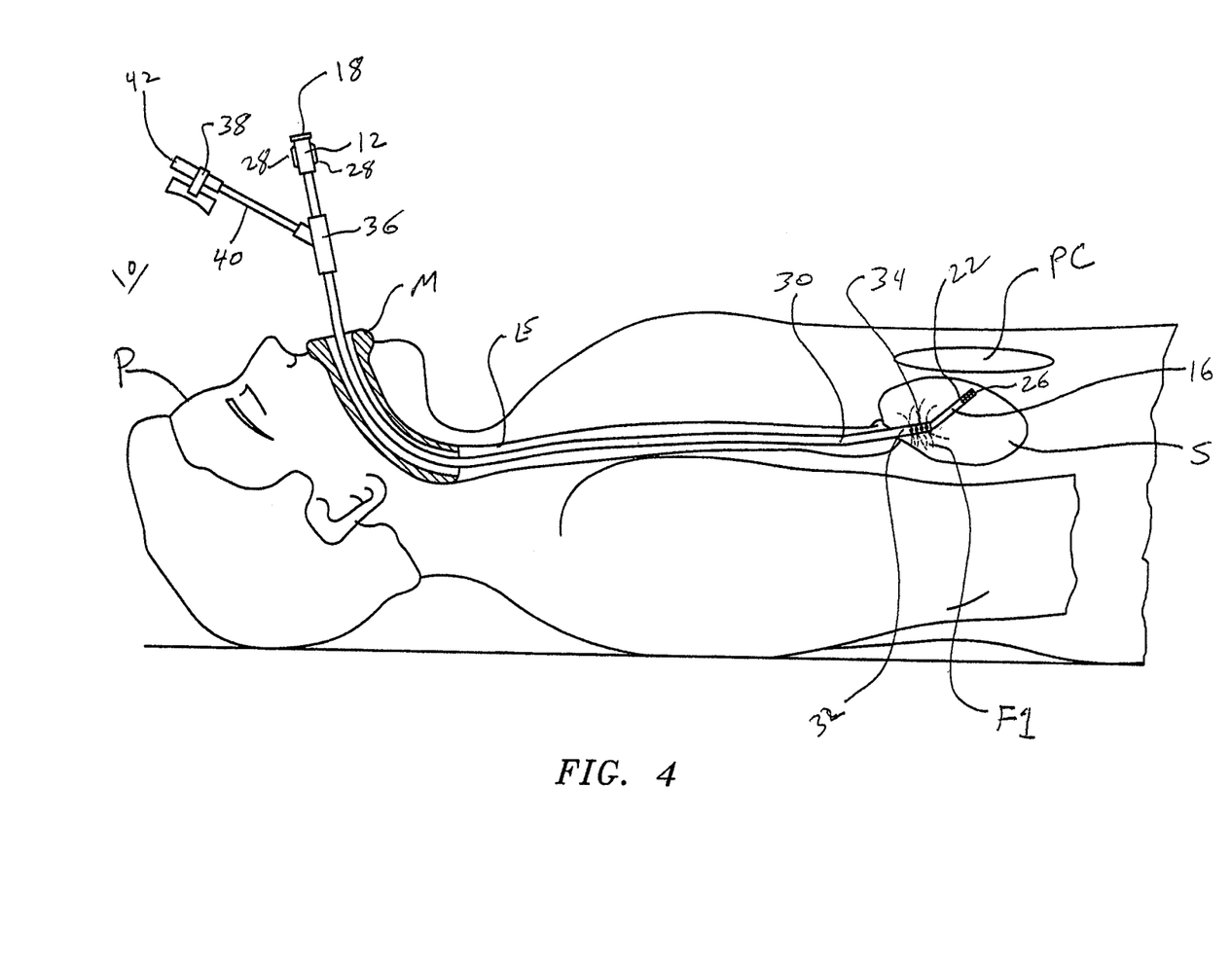
FIG. 4 is a perspective view, partially shown in section, illustrating the embodiment of FIG. 1 initially inserted into a patient.
Figure 5:
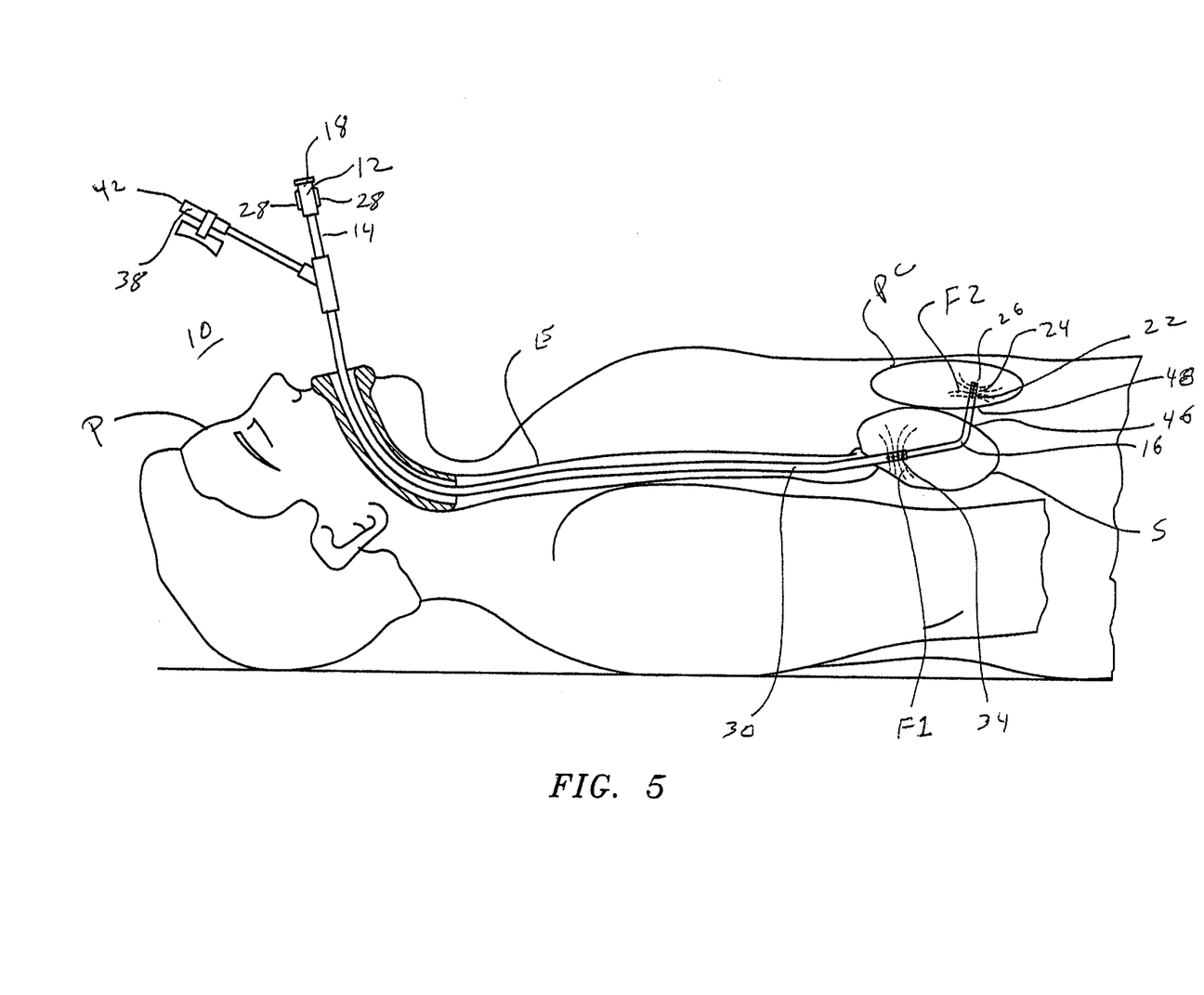
FIG. 5 is a perspective view, similar to FIG. 4, illustrating the operating end of the catheter positioned within the peritoneal cavity of the patient.

Referring to FIGS. 4 and 5, and initially with regard to FIG. 4, the use of catheter 10 in endoluminal surgery to access the peritoneal cavity through the stomach will now be described. Initially, catheter 10 is inserted through the mouth M of a patient P and advanced through the esophagus E so as to position distal end 22 of inner tube 16, as well as distal end 32 of outer tube 30, within the stomach S of the patient. Once catheter 10 has been so positioned, a first source of insufflation fluid (not shown) may be attached to a valve system 38 and actuated to force a first inflation fluid F1 through inflation lumen 42 and out inflation ports 34 in outer tube 30 in order to insufflate stomach S. The first source of inflation fluid may provide various auxiliary functions such as, for example, providing for pressure measurement so as to maintain constant pressure within the stomach, etc. While the present procedure is being described as insufflating stomach S prior to penetration of the stomach and the peritoneal cavity and insufflation of the peritoneal cavity, insufflation of stomach S may be delayed until after one or more of these steps have been accomplished.

With continued reference to FIG. 4, catheter 10 is then further advanced through the esophagus E to cause cutting edge 26 at distal end 22 of inner tube 16 to engage and puncture stomach S.

Referring now to FIG. 5, continued advancement of catheter 10 through esophagus E causes cutting edge 26 to form a hole 46 through stomach S and a hole 48 in peritoneal cavity PC to position distal end 22 of inner tube 16 within peritoneal cavity PC. Thereafter, a second source of inflation fluid (not shown) is connected to hub 12 and actuated to force a second inflation fluid F2 through operative lumen 18 so as to insufflate peritoneal cavity PC. Once peritoneal cavity PC has been insufflated, operative lumen 18 is used as the access passageway for the insertion of instruments into peritoneal cavity PC to perform any of various surgical procedures. It should be noted that, during the performance of the surgical procedures, the fluid pressure within stomach S due to inflation fluid F1 prevents the flattening or collapse of stomach S due to the inflation pressure in the peritoneal cavity PC and the activities of the surgical procedures being conducted therein. As with the first source of inflation fluid described hereinabove, the second source of inflation fluid might also be provided with auxiliary functions such as, for example, pressure measurement, pressure monitors and control devices, etc. in order to manage and adjust any losses in inflation pressure within peritoneal cavity PC during the surgical procedure.

It should be further noted that the disclosed catheter 10 and disclosed surgical method allows the surgeon to precisely control the pressures within peritoneal cavity PC and stomach S concurrently.

While not specifically shown, it is also contemplated that catheter 10 may be provided with the various anchoring and or sealing structures, such as, for example anchoring or sealing balloons adjacent distal ends 22 and 32 of inner tube 16 and outer tubes 30, respectively. This will assist in preventing movement of catheter 10 during the surgical procedures as well as preventing leakage and/or transfer of inflation fluids between stomach S and peritoneal cavity PC.

Figure 6:
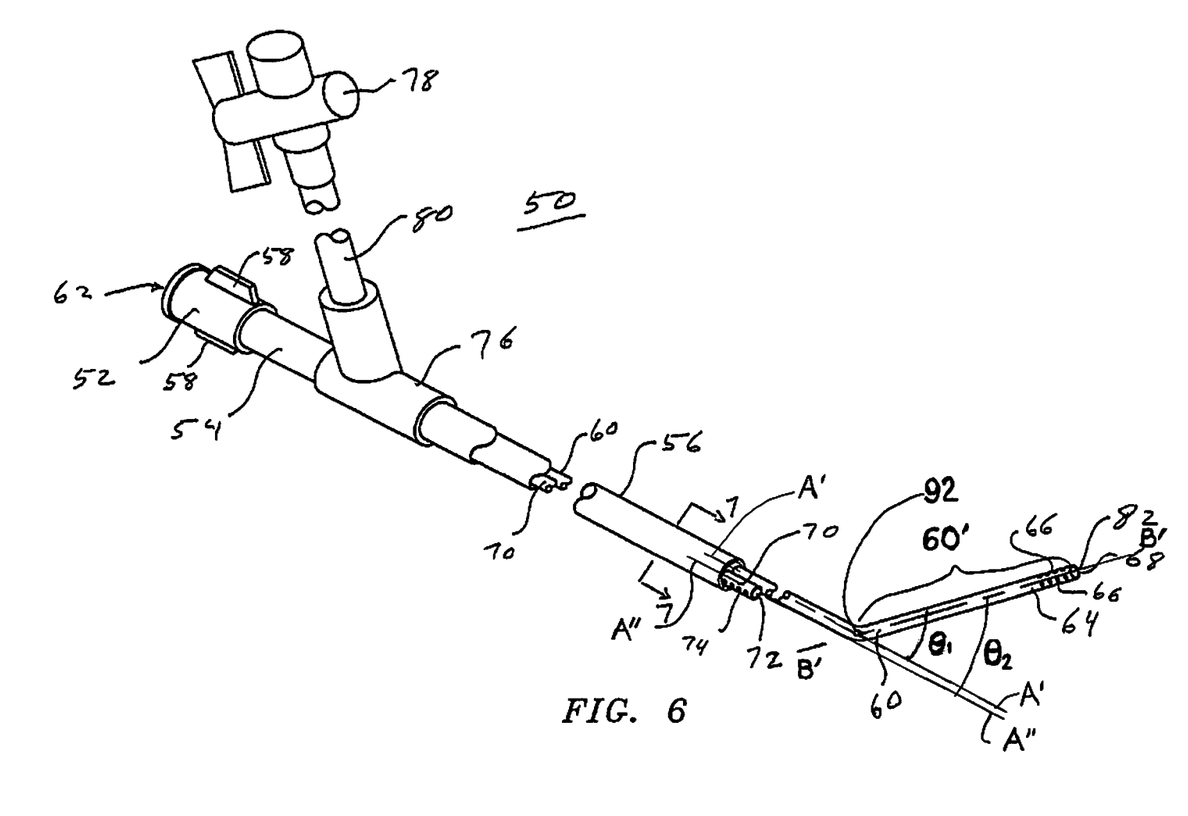
FIG. 6 is a perspective view of an alternative embodiment of a duel lumen catheter for use in minimally invasive endoluminal surgery.

Referring now to FIG. 6, there is disclosed in alternative embodiment of a dual lumen catheter 50. In contrast to dual lumen catheter 10 described hereinabove, the operative and inflation lumens of catheter 50 are parallel but not concentric as was the case with dual lumen catheter 10. Catheter 50 generally includes a hub 52 having an outer sheath 54 extending distally therefrom. A support tube 56 extends through hub 52 and outer sheath 54 and encases the operative and inflation lumens of catheter 50 as described in more detail hereinbelow. Hub 52 is provided with a pair of wings 58 to facilitate manipulation of catheter 50 through the body of a patient.

A distal tube 60 extends through hub 52, outer sheath 54 and support tube 56 to define a longitudinal axis N-A'. A proximal end 62 of distal tube 60 is positioned adjacent hub 52 while a distal end 64 of distal tube 60 is provided with a plurality of ports 66. A cutting edge 68 may be provided on distal end 64 to facilitate puncturing of the stomach and the peritoneal cavity.

A proximal tube 70 extends partially through sheath 54 and through support tube 56. Proximal tube 70 has a sealed distal end 72 and a plurality of ports 74 adjacent sealed distal end 72. A T-collar 76 surrounds sheath 54 and is in fluid communication with ports 74 in proximal tube 70. A valve system 78 is provided to receive of source of fluid and is connected to T-collar 76 by a fluid tube 80.

Figure 7:
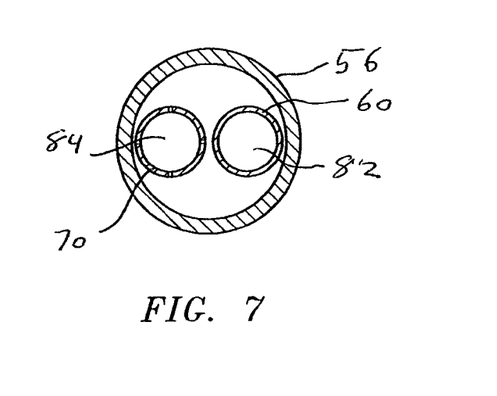
FIG. 7 is a cross-sectional view taken along lines 7-7 of FIG. 6.

Distal tube 60 defines an operative lumen 82 extending from proximal end 62 to distal end 64. As best shown in FIG. 7, inner tube 70 defines an inflation lumen 84. Distal tube 60 and proximal tube 70, and thus operative lumen 82 and inflation lumen 84, extend through support tube 56 in parallel, but not concentric, fashion. The distal tube 60 extends at least to a position 92 that is distal from the sealed end 72 of the proximal tube 70 to define the longitudinal axis A'-A'. The distal end 64 of the distal tube 60 defines a portion 60' of the distal tube 60 that extends at least from position 92 to define an offset axis B'-B' with respect to the longitudinal axis A'-A'. Additionally, the sealed distal end 72 of proximal tube 70 extends through hub 52, outer sheath 54 and support tube 56 to define a longitudinal axis A"-A" along the proximal tube 70. Since the distal tube 60 and proximal tube 70, and thus operative lumen 82 and inflation lumen 84, extend through support tube 56 in parallel fashion, the longitudinal axes A'-A' and A"-A" are also parallel to each other.

The offset axis B'-B' of the portion 60' of the distal tube 60 defines an offset angle $\theta_1$ with respect to the longitudinal axis A'-A' of the distal tube 60. The offset axis B'-B' also defines an offset angle $\theta_2$ with respect to the longitudinal axis A"-A" of the proximal tube 70. When the two longitudinal axes A'-A' and A"-A" are precisely parallel, the offset angles $\theta_1$ and $\theta_2$ are equal. Consequently, the radially oriented insufflation ports 66 in proximity to the distal end 64 of the distal tube 60 are positioned at a position that is offset from the radially oriented insufflation ports 74 at the sealed distal end 72 of the proximal tube 70.

Figure 8:
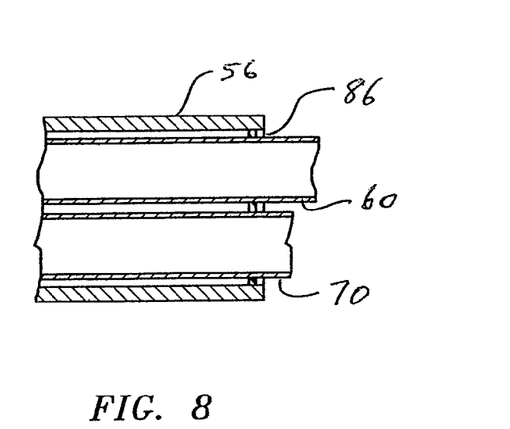
FIG. 8 is a cross-sectional view taken at the junction of an outer sheath with the inner lumens.

Referring for the moment to FIG. 8, both distal tube 60 and proximal tube 70 extend beyond support tube 56. A seal 86 is provided within support tube 56 and about distal tube 60 and proximal tube 70 to prevent the influx of any fluids or other matter within support tube 56 during a surgical procedure.

Figure 9:
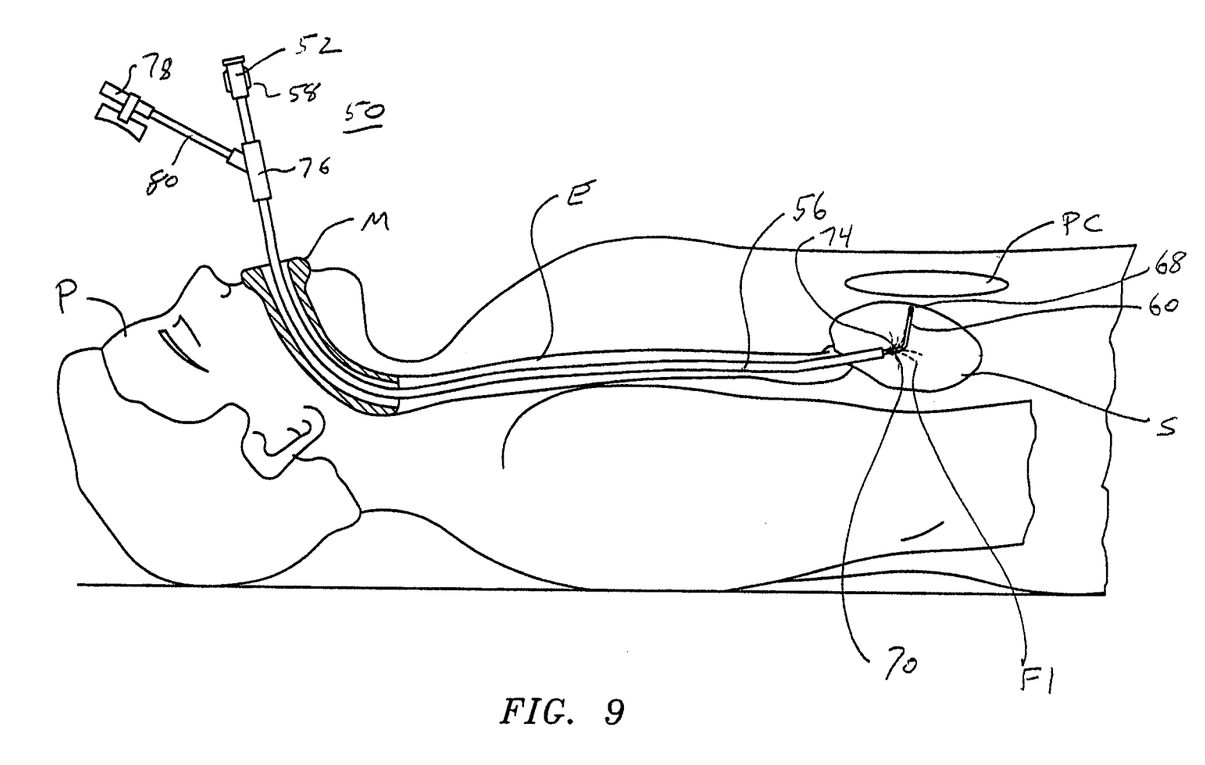
FIG. 9 is a perspective view, partially shown in section, illustrating the embodiment of FIG. 6 initially inserted into a patient.
Figure 10:
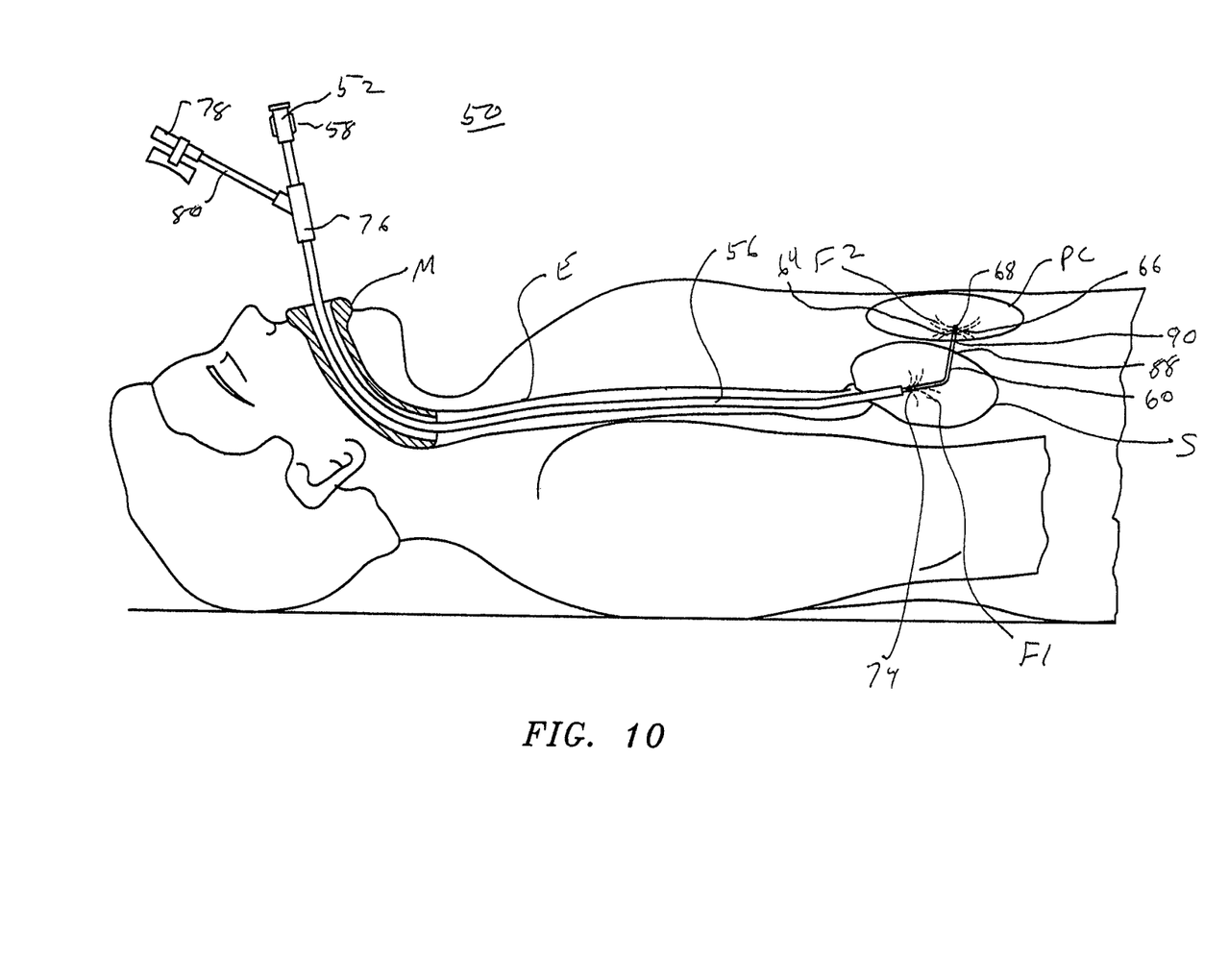
FIG. 10 is a perspective view, similar to FIG. 9, illustrating the operating end of the catheter positioned within the peritoneal cavity of a patient.

Referring to FIGS. 9 and 10, and initially with regard to FIG. 9, the use of catheter 50 in endoluminal surgery to access the peritoneal cavity through the stomach will now be described. The following procedure is substantially identical to that described hereinabove with respect to catheter 10. Initially, catheter 50 is inserted through the mouth M of a patient P and advanced through the esophagus E so as to position in distal end 64 of distal tube 60 as well as distal end 72 of proximal tube 70 within stomach S of the patient. Once catheter 50 has been so positioned, a first source of insufflation fluid (not shown) may be attached to a valve system 78 and actuated to force a first inflation fluid F1 through inflation lumen 84 and out inflation ports 74 in proximal tube 70 in order to insufflated stomach S. As above, the first source of inflation fluid may provide various auxiliary functions such as, for example, providing for pressure measurement so as to maintain constant pressure within the stomach, etc. While the present procedure is being described as insufflated stomach S prior to penetration of the stomach and the peritoneal cavity and insufflation of the peritoneal cavity, insufflation of stomach S may be delayed until after one or more of these steps have been accomplished.

With continued reference to FIG. 9, catheter 50 is then further advanced through the esophagus E to cause cutting edge 68 at distal end 64 of distal tube 60 to engage and puncture stomach S.

Referring now to FIG. 10, continued advancement of catheter 50 through esophagus E causes cutting edge 68 to form a hole 88 through stomach S and a hole 90 in peritoneal cavity PC to position distal end 64 of distal tube 60 within peritoneal cavity PC. Thereafter, a second source of inflation fluid (not shown) may be connected to hub 12 and actuated to force a second inflation fluid F2 through operative lumen 82 so as to insufflate peritoneal cavity PC. Once peritoneal cavity PC has been insufflated, operative lumen 82 is used as the access passageway for the insertion of instruments into peritoneal cavity PC to perform any of various surgical procedures. As noted hereinabove, the fluid pressure within stomach S due to inflation fluid F1 prevents the flattening or collapse of stomach S due to the inflation the peritoneal cavity PC and the activities of the surgical procedures being conducted therein. As with the first source of inflation fluid described hereinabove the second source of inflation fluid might also be provided with auxiliary functions such as, for example, pressure measurement, pressure monitors and control devices, etc. in order to manage and adjust any losses in inflation pressure within peritoneal cavity PC during the surgical procedure.

It should be further noted that the disclosed catheter 50 and the disclosed surgical method allow the surgeon to precisely control the pressures within peritoneal cavity PC and stomach S concurrently.

While not specifically shown, it is also contemplated that catheter 50, similar to catheter 10 described hereinabove, may be provided with the various anchoring and or ceiling structures, such as, for example anchoring or sealing balloons adjacent distal ends 64 and 72 of distal tube 60 and proximal tube 70, respectively. This will assist in preventing movement of catheter 50 during the surgical procedures as well as preventing leakage and/or transfer of inflation fluids between stomach S and peritoneal cavity PC.

It will be understood that various modifications may be made to the embodiments disclosed herein. For example, additional lumens may be provided through the disclosed catheters to provide for auxiliary instruments such as, for example, endoscopes, etc. Further, as noted hereinabove, various anchoring and/or sealing structures may be provided on the disclosed tubes to prevent leakage as well as movement of the catheter within the body of the patient. Additionally, various known types of fluid sources and auxiliary devices for maintaining and monitoring pressure through the various lumens and within the various cavities in the body of the patient may be provided. Therefore, the above description should not be construed as limiting, but merely as exemplifications of particular embodiments. Those skilled in the art will envision other modifications within the scope and spirit of the claims appended hereto.

The invention claimed is:

1. A method of performing a minimally invasive procedure utilizing a dual lumen catheter comprising:

provided a catheter having a first tube defining an operative lumen having radially oriented insufflation ports enabling insufflation via said operative lumen and a second tube extending parallel to the first tube and circumferentially sealed at the distal end of the second tube, the distal end of the second tube being positioned proximally of the distal end of the first tube, the second tube defining an inflation lumen having radially oriented insufflation ports and terminating proximally of the distal end of the first tube such that a fluid flowing through the second tube defining the inflation lumen exits only through the radially oriented insufflation ports, the first tube extending at least to a position distal from the distal end of the second tube to define a longitudinal axis extending at least to the position distal from the distal end of the second tube, the distal end of the first tube defining a portion of the first tube extending at least from the position distal from the distal end of the second tube to define an offset axis with respect to the longitudinal axis of the first tube, the offset axis defining an offset angle with respect to the longitudinal axis of the first tube;

inserting the catheter through the esophagus of a patient so as to position a distal end of the second tube within the stomach of a patient such that a fluid flowing through the second tube exits into the stomach only through the radially oriented insufflation ports;

advancing the catheter through the esophagus of a patient such that the radially oriented insufflation ports at the distal end of the first tube are positioned at a position offset from the radially oriented insufflation ports at the distal end of the second tube; and performing a surgical operation through the first tube.

2. The method as recited in claim 1, further comprising the step of pressurizing the interior of the stomach by forcing a fluid through the inflation lumen.

3. The method as recited in claim 1, further comprising the step of pressurizing an area outside of the stomach by forcing a fluid through the operative lumen.

4. The method as recited in claim 1, further comprising the step of puncturing the wall of the stomach with the distal end of the first tube.

* * * * *